United States Patent
Parton

[11] Patent Number: 5,834,197
[45] Date of Patent: Nov. 10, 1998

[54] METHODS OF CAPTURING SPECIES FROM LIQUIDS AND ASSAY PROCEDURES

[75] Inventor: Adrian Parton, Exning, United Kingdom

[73] Assignee: Genera Technologies Limited, Cambridge, United Kingdom

[21] Appl. No.: 737,296

[22] PCT Filed: May 10, 1995

[86] PCT No.: PCT/GB95/01056

§ 371 Date: Nov. 8, 1996

§ 102(e) Date: Nov. 8, 1996

[87] PCT Pub. No.: WO95/31726

PCT Pub. Date: Nov. 23, 1995

[30] Foreign Application Priority Data

May 11, 1994 [GB] United Kingdom .................. 9409348
Nov. 25, 1994 [GB] United Kingdom .................. 9423867

[51] Int. Cl.[6] ...................................... C12Q 1/68
[52] U.S. Cl. .............................. 435/6; 209/213; 209/214; 210/695; 210/222; 422/101; 435/7.1; 435/7.2; 435/7.22; 435/7.32; 435/7.5; 435/7.92; 435/29; 435/803; 436/518; 436/526; 436/806; 436/824
[58] Field of Search ................................. 209/213, 214; 210/695, 222; 252/62.51; 422/50, 101; 75/255; 435/6, 7.1, 7.2, 7.22, 7.32, 7.5, 7.92, 29, 174, 239, 803; 436/518, 526, 806, 807, 824

[56] References Cited

U.S. PATENT DOCUMENTS

| | | |
|---|---|---|
| 3,917,538 | 11/1975 | Rosensweig . |
| 4,157,323 | 6/1979 | Yen et al. . |
| 4,554,088 | 11/1985 | Whitehead et al. . |
| 4,732,811 | 3/1988 | Margel . |
| 5,385,707 | 1/1995 | Miltenyi et al. .......................... 422/69 |

FOREIGN PATENT DOCUMENTS

| | | |
|---|---|---|
| 125 995 | 11/1984 | European Pat. Off. . |
| 184 710 | 6/1986 | European Pat. Off. . |
| 230 768 | 8/1987 | European Pat. Off. . |
| 93/10162 | 5/1993 | WIPO . |
| 93/16383 | 8/1993 | WIPO . |
| WO 94/11078 | 5/1994 | WIPO . |

OTHER PUBLICATIONS

Clinica Chimica Acta,69 (1976) 387–396, Solid–Phase, Magnetic Particle Radioimmunoassay, Lynn Nye et al. (See Appln. p. 5).

Clinical Chemistry, vol. 26, No. 9, 1980, Magnetizable Solid–Phase Fluoroimmunoassay of Phenytoin in Disposable Test Tubes, pp. 1281–1284, R.S. Kamel et al. (See Appln. p. 5).

Journal of Immunological Methods 53 (1982) pp. 109–122 Albumin Magnetic Microspheres: A Novel Carrier for Myelin Basic Protein, Haim Ovadia et al. (See Appln. p. 5).

Biotechnology and Bioengineering, vol. XIX, pp. 101–124 (1977)Nonporous Magnetic Materials As Enzyme Supports-:Studies with Immobilized Chymotrypsin, P.A.Munro et al.

Primary Examiner—Susan Wolski
Attorney, Agent, or Firm—Cushman Darby & Cushman IP Group of Pillsbury Madison & Sutro LLP

[57] ABSTRACT

A species such as a microorganism, e.g. Legionella, Giardia or Cryptosporidium, is captured by first attracting plastic coated magneticbeads or other magnetically attractable particles to a solid support such as stainless steel mesh, which particles have a selective affinity for the species, e.g. by virtue of an antibody coating, and contacting a sample containing the species with the particles on the solid support. The beads bearing the captured species may be released by reduction of the magnetic attraction of the support for the beads, e.g. by turning off an electromagnet used to magnetize the support.

11 Claims, 2 Drawing Sheets

METHODS OF CAPTURING SPECIES FROM LIQUIDS AND ASSAY PROCEDURES

This application is the national phase of international application PCT/GB95/01056 filed May 10, 1995 which designated the U.S.

The present invention relates to methods of capturing species from liquids and to assay procedures involving said species.

Whilst the present invention is of broad and general applicability, it has particular relevance to the problem of monitoring organisms in water and will be described with particular reference to that context.

Current methods for assaying the content of organisms in water such as cryptosyporidium and giardia are time consuming and labor intensive.

A major problem in such assay procedures is that the organisms may be present in very low numbers in substantial volumes of water and must first be concentrated into a sample of substantially reduced volume. Conventionally, this is done by passing large volumes of water through a cellulosic filter material which is then broken up and placed in a smaller volume of liquid in which it is agitated over a prolonged period with a view to releasing the captured organisms from the filter material. The proportions of organisms present in the liquid samples which are captured by this way and successfully released from the filter material is relatively poor and the operation is prolonged taking typically about twenty-four hours to perform. The product of this procedure is a sample in which the organisms are still very dilute.

In WO 93/16383, an assay for cryptosyporidium oocysts by an electrorotation assay technique is described, which requires direct visualization of the oocysts under a microscope. To run such an assay on water samples of the kind normally encountered requires further concentration of the organisms beyond the stage reached following the filtration procedure described above.

In unrelated assay procedures, it is known that magnetically attractable particles may be coated with selective reagents such as antibodies or oligonucleotides. Such coated magnetically attracted particles are used in assay procedures by mixing the particles in suspension with a species to be captured so as to form a complex in which the species is captured to the particles. The magnetic particles are then collected by magnetic attraction so as to concentrate and localise the captured species for further operations.

The present invention now provides a method of capturing a species from a liquid comprising attracting magnetically attractable particles to a solid support by magnetic forces, which particles have an affinity for said species, and contacting said particles on said support with said liquid to capture said species on to said particles on said solid support by reduction of said magnetic forces.

Because the particles are held on the solid support during the time in which they are being contacted with the liquid containing the species to be captured, it is possible for the volume of liquid containing the species to be much greater than the volume occupied by the particles during this operation. Large volumes of the liquid may be washed through or over the solid support bearing the magnetically attracted particles, so that the particles may capture said species in sufficient quantity for further operations to be carried out, even if the species is present at great dilutions in the liquid. For instance, the volume of the liquid contacted with the particles may be greater than the volume occupied by the solid support by a factor of at least 10, more preferably from to 100 or more.

The liquid may be passed repeatedly over the solid support, e.g. by continuous recirculation, so as to improve the capture of said species.

The particles may be assayed for the captured species whilst retained on the solid support. It will generally however be more appropriate to release the particles with the captured species. This may be done simply by vigorous washing or even air blasting whilst maintaining the magnetic attraction but is preferably accomplished by reducing the magnetic attraction.

When the particles are released from the solid support, they may be collected in a much reduced volume of liquid, for instance a volume similar to that occupied by the solid support itself, or even less.

A very substantial concentration of the species to be captured may therefore be achieved.

We have found that the same result cannot be achieved by the alternative procedure of mixing the magnetically attractable particles with the sample to form complexes between the particles and the species to be captured and then passing the resulting dilute suspension of complexed particles through a zone of magnetic attraction to capture them. The process of magnetic attraction of the particles is too slow and too easily disrupted by liquid currents and the formation of the required complexes in the volume of a dilute sample would require an excessive concentration of magnetically attractable particles.

The solid support may be a superparamagnetic material or ferromagnetic material. "Superparamagnetism" is the magnetic behaviour exhibited by materials which respond to a magnetic field with an induced magnetic field without resultant permanent magnetisation.

There are many examples of materials which exhibit superparamagnetism or ferromagnetism which may be used in the present invention. Particularly preferred materials are stainless steel, aluminium, chromium or platinum. Metallized foams based on such metals may be used, e.g. aluminium coated polyester/polyether foams which are commercially available.

However, materials in which an induced magnetic field results in a permanent residual field may also be used as further described below.

A solid support material may be magnetized to attract the magnetically attractable particles by placing the solid support within a suitable container and applying an external magnetic field from a permanent magnet or an electromagnet. The solid support, if of superparamagnetic material, may be demagnetized simply by turning off the electromagnet or physically removing the permanent magnet used so as to reduce the field. The magnetic field applied may be a rapidly reversing magnetic field obtained by passing an alternating current through a coil.

Preferably, to prevent heat generated in the coil of an electromagnet used for this purpose from reaching the solid support, the solid support may be positioned in a pole gap of a magnet core about which core a coil winding is positioned remote from the solid support.

A solid support material which is not superparamagnetic may be demagnetized by known methods such as gradual reduction and periodic reversal of an externally applied field.

Physically, the solid support may take many forms e.g. mesh, wire, a wool, beads or one or more plates. The material preferably has an open structure to assist easy removal of the particles therefrom and easy passage on the liquid containing the species to be captured. Structures providing a substantial surface area within a small volume are preferred.

However, the solid support may simply be the walls of a container such as a glass tube to which the particles are attracted by an external magnetic field.

The most preferred form of solid support is a stainless steel mesh, e.g. of 40×40 wires per inch (16×16 wires per cm), used as a flat strip of single or double thickness.

Many forms of magnetically attractable particle are now known and easily commercially available. Examples include iron oxide particles as described in U.S. Pat. No. 4,554,088 and U.S. Pat. No. 3,917,538, nickel oxide particles as described in Biotec. and Bioengr. XIX: 101–124 (1977), Agarose-polyaldehyde beads containing magnetic particles as in U.S. Pat. No. 4,732,811, DYNAL beads (commercially available magnetic polystyrene coated beads); Magnogel 44 (magnetic polyacrylamide-agarose beads), ENZACRY (poly-M-diaminobenzene/iron oxide) as described in Clin. Chim. Acta. 69:387–396 (1976). Cellulose containing ferric oxide particles are described in Clin. Chem. 26:1281–1284 (1980) and albumin magnetic microspheres as described in J.IMMUNOL. Methods 53:109–122 (1982). Magnetic porous glass particles are described in WO-A-93/10162.

The particles may also be of superparamagnetic material.

The particles may preferably have a specific binding affinity for the species to be captured and for this purpose they may bear antibody molecules, substances having an epitope capable of reacting in a specific manner with an antibody such as an antigenic protein or oligosaccharide, biotin, avidin or streptavidin, or like materials. They may bear a nucleic acid or nucleic acid analogue such as DNA, RNA or a synthetic analogue thereof. Also, the particles may have a chemical rather than a biochemical affinity for the species to be captured. For instance, they may have chelating activity for capturing ions from the liquid.

They may have affinity for a water borne organism such as Legionella, cryptosyporidium or giardia. However, the invention is of general applicability and may be used for capturing a wide range of micro-organisms from a wide range of sample sources including food products and body fluid samples such as blood, serum, saliva, urine, cerebrospinal fluid and so forth.

The invention includes assay methods comprising capturing a species to be assayed or to be used in an assay by a method of capture as described above, and conducting an assay of or using said captured species. Optionally, the captured species may be removed from the particles prior to or during said assay procedure.

The assay procedures involved may take a wide variety of forms including chemical assay procedures, enzyme assay procedures such as RIA or ELISA or nucleic acid procedures such as hybridization assays.

Preferably however, the assay is an electro-rotation assay. WO-A-93/16383 describes apparatus in which electro-rotation assays can be conducted. As described there, particles such as plastics microbeads or the cells of organisms like giardia and cryptosyporidium can be made to rotate by the application of a rotating electrical field. The field conditions under which rotation is achieved, the direction of rotation and the speed of rotation, all depend upon the dielectric properties of the particle. Microorganism cells such as cryptosyporidium oocysts can be concentrated by a capture method as described above and can then be detected by subjecting them to electro-rotation conditions and observing their electro-rotation. The magnetically attractable particles used in the concentration of the oocysts need not be removed prior to electro-rotation and indeed are an aid in observing the rotation, particularly where automated image analysis systems are used to perform the observation. The particle or particles bound to the oocysts provide a useful visual marker which can be seen rotating.

The invention includes apparatus for use in capturing a species from a liquid comprising a reservoir for said liquid, a source of magnetic field, a pump for liquid circulation and means defining a flow path for liquid from said reservoir via said pump and back to said reservoir, wherein said source of magnetic field is outside said flow path and said flow path contains a solid support magnetizable by a magnetic field applied thereto by said source of magnetic field.

The invention further includes apparatus for use in capturing a species from a liquid, comprising a conduit for flow therethrough of said liquid, a solid support in said flow path in which a magnetic field can be induced, a source of magnetic field out-side said conduit for inducing a magnetic field in said solid support, and magnetically attractable particles on said solid support which have an affinity for a said species.

The invention will be further described and illustrated with reference to the accompanying drawing in which.

Figure 1:
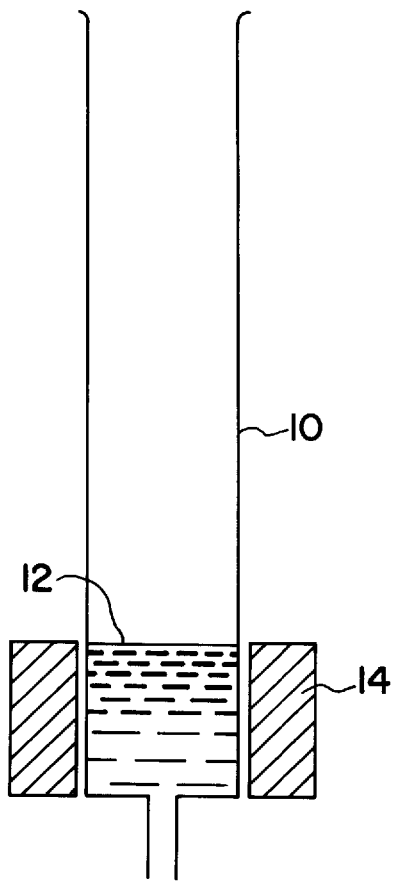
FIG. 1 shows schematically apparatus for use in the invention.

As shown in FIG. 1, apparatus for use in the invention may comprise a container such as a syringe body 10 containing a support matrix such as expanded aluminium 12 surrounded by a helically wound copper wire coil 14 which may for instance comprise 4000 turns of enamelled 40 SWG (standard wire gauge) wire to which is connected a suitable supply of alternating electric current e.g. a 50 volt 50 Hz supply, via suitable switch means. Generally, frequencies of from 1 to 500 volts may be employed at voltages of from 1 to 500 volts.

In a typical procedure according to the invention, antibody coated magnetic beads in a suitable buffer (e.g. pbs) are exposed to the solid support and an external magnetic field is applied to induce a corresponding field in the solid support. Over a period of minutes, the particles are drawn on to the solid support. The attached particles may be washed by slowly running wash liquid into the top of the syringe body 10 whilst letting liquid out at a corresponding rate so as to avoid the level of liquid falling to expose the solid support. If this were to happen, there would be a likelihood of surface tension forces pulling the beads off.

A sample containing organisms expressing surface antibodies corresponding to the antibodies in the beads and having a volume which may be of the order of 100 times the volume of the part of the syringe body 10 occupied by the solid support 12 may then be slowly run through, optionally followed by further wash liquid, until the solid support is barely covered.

The external magnetic field is then removed and the beads are permitted to detach from the solid support, optionally with agitation being used to disperse them. The beads may then be run out of the syringe for analysis, bearing any organisms which have bound thereto. An advantage of this procedure is that there is no need to use any chemical treatment to release the organisms from the solid support, which could affect the viability or integrity of the organisms. Chemical methods are, in contrast, normally needed in most immuno-affinity capture and release methods.

Figure 2:
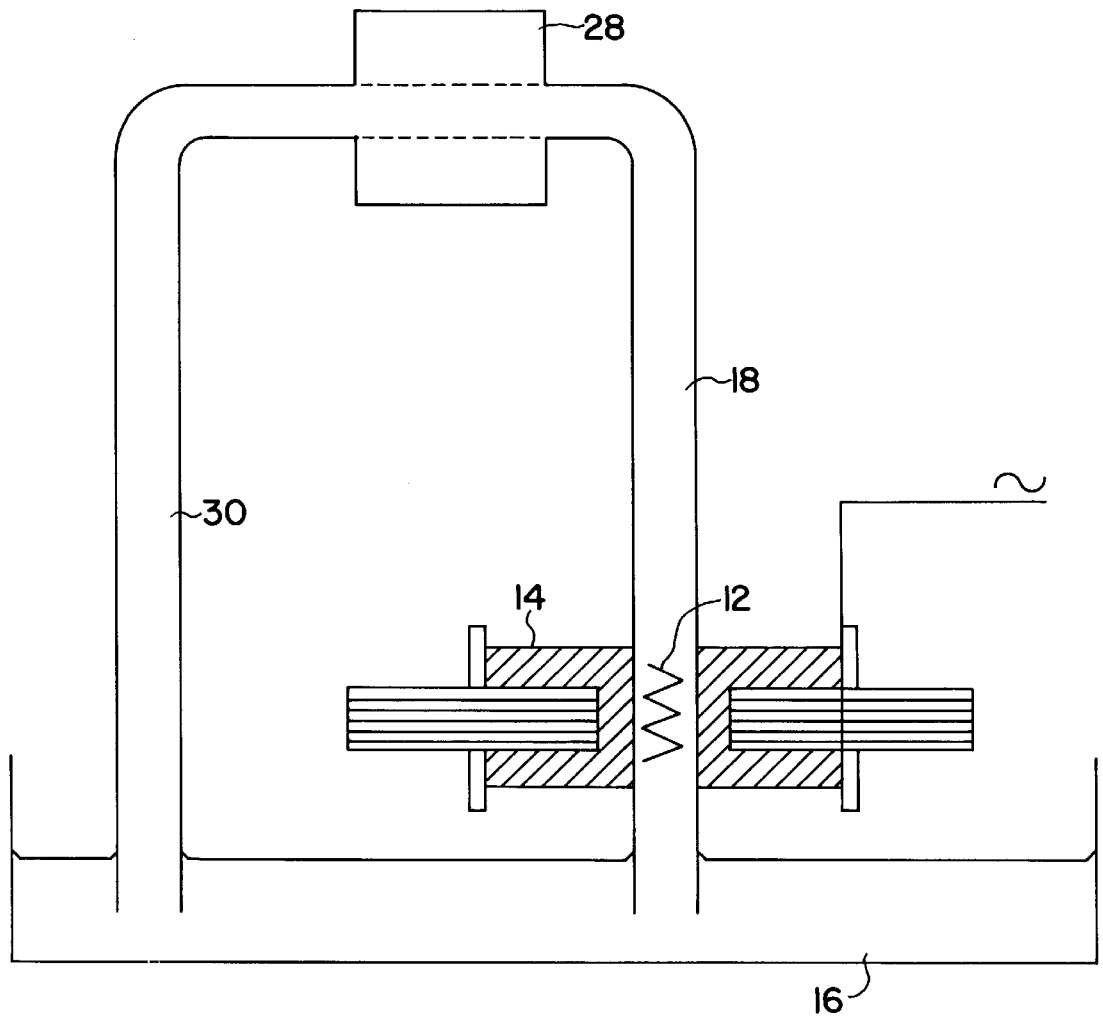
FIG. 2 shows a second form of apparatus for use in the invention.

An alternative form of apparatus shown in FIG. 2 comprises a reservoir 16 for liquid. A tube 18 dipping into the reservoir 16 contains the solid support 12. As shown in FIG.

3, the tube passes through a pole gap 20 in a magnet core 22 which is C-shaped in plan view having a long arm 24 remote from the pole gap 20 around which is positioned a coil 14 wound on a coil former bobbin 26 and connected to an electrical supply as described in connection with FIG. 1. The tube 18 is connected via a peristaltic pump 28 to a further tube 30 dipping back into the reservoir 16.

In use, liquid to be treated in the system may be recirculated repeatedly using the peristaltic pump 28 to flow over the solid support valve as described in more detail in Example 2 below.

The invention will also be further illustrated by the following examples.

EXAMPLE 1

Super-paramagnetic polystyrene beads containing magnetite (average diameter 0.8 μm, 67% magnetic content—Sigma Chemical Co.) were coated overnight at room temperature with a mouse monoclonal antibody raised against cryptosporidium. The resultant antibody coated beads were placed into an apparatus similar to that shown in FIG. 1 and described in the above text.

An A/C field (50 Hz, 50 volts) was applied to the coil to generate a magnetic field, and the beads were incubated with the aluminium solid phase for 6 minutes. Following this incubation, excess unbound beads were washed away with PBS (phosphate buffered saline).

A 10 ml sample containing cryptosporidium oocysts (obtained from Moredum Institute Animal Health) was added to the tube and incubated for 10 minutes (in the presence of the applied magnetic field).

After incubation, the solid phase was washed/rinsed with 10 ml of PBS whilst the magnetic field was present.

Following washing, the magnetic field was removed, i.e. field generator was switched off; and the magnetic bead/crypto were flushed out in 1 ml of PBS.

The presence of cryptosporidium/bead complexes was determined by immuno-fluorescence staining techniques using an anti-cryptosporidium fluorescent FITC conjugate (Bradsure Biochemicals Ltd.). Cryptosporidium complexes were detectable using the procedure clearly indicating that specific capture and the subsequent elution (from the solid phase) had been achieved.

EXAMPLE 2

Figure 3:
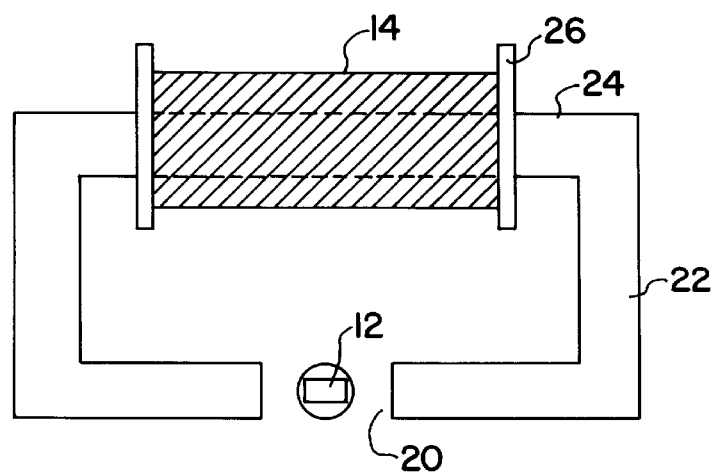
FIG. 3 is a plan view of the electromagnet in the apparatus shown in FIG. 2.

Using the apparatus described above with reference to FIGS. 2 and 3, 50 ml PBT (phosphate buffered saline+0.05% Tween 20) was circulated over the solid support at a flow rate of approximately 100 ml/30 sec. The solid support was a thin strip of stainless steel formed into the zig-zag configuration illustrated in FIG. 2. A suspension of antibody coated beads (200 μl) was added to the reservoir and the electrical power was turned on at 50 volts/50 Hz. Circulation was continued for 45 minutes.

Most of the PBT was drained off from the reservoir and 100 ml of fresh PBT was added as a wash.

A spike of cryptosporidium oocysts in a volume of 50 ml PBT was added and allowed to circulate for 45 minutes. The bulk of this was then drained off from the reservoir and 100 ml of fresh PBT was added as a further wash. This wash liquid was drained off and combined with the remainder of the 50 ml spike liquid for later determination of the cryptosporidium remaining in the circulating liquid.

The solid support was further washed with 400 ml PBT. Circulation was then halted. The power was turned off from the magnet and the cryptosporidium was eluted from the solid phase using 5 ml PBS. This eluate was collected for determination of the numbers of cryptosporidium occysts captured.

To determine the number of oocysts present, the liquid was in each case pushed through a membrane filter which was then stained and the numbers of oocysts determined by immuno-fluorescence. The results are as shown in the table below:

| Run | Oocysts not Captured | Oocysts Captured and Recovered | Percent Captured and Recovered |
| --- | --- | --- | --- |
| 1 | 272 | 352 | 56 |
| 2 | 218 | 316 | 59 |
| 3 | 374 | 559 | 60 |

EXAMPLE 3

Determination of Capture Efficiency of Cryptosporidium oocysts.

The apparatus described above with reference to FIGS. 2 and 3 was modified by substituting as the solid support a 1 cm×3 cm strip of stainless steel mesh (40×40 wires per inch (16×16/cm)) folded longitudinally in half to make a double thickness strip 0.5 cm wide. PBT (Phosphate Buffered Saline+0.05% Tween 20) (25 ml) was circulated over the solid support at a flow rate of approximately 100 ml/30 seconds. A suspension of antibody coated beads specific to Cryptosporidium (500 μl) was added to the reservoir and the electrical power was turned on at 60 volts/50 Hz. Circulation was continued for 60 minutes and current adjusted to 75 mA. Following this, excess beads were run to waste together with a 20 ml wash of PBT. The beads were as described in Example 1.

A spike of Cryptosporidium oocysts of known number in 25 ml was added to the reservoir and allowed to circulate for 60 minutes. At the end of this period, the solid support was washed by running through 500 ml of PBT to waste. The flow was then halted and the Cryptosporidium bead complexes eluted from the solid phase using 20 ml PBS. This eluate was collected for determination of numbers of Cryptosporidium oocysts captured. To determine the number of oocysts present, the liquid in each case was pushed through a membrane filter which was then stained and the numbers of oocysts determined by immunofluorescence. The results are shown in the table below:

| Run | Oocysts | Oocysts Captured and Recovered | Percent Captured and Recovered |
| --- | --- | --- | --- |
| 1 | 515 | 163 | 31.6% |
| 2 | 390 | 162 | 41.5% |
| 3 | 502 | 232 | 46.2% |

EXAMPLE 4

Determination of Capture Efficiency of Giardia oocysts.

Using the apparatus as used in Example 3, 25 ml PBT (Phosphate Buffered Saline+0.05% Tween 20) was circulated over the solid support at a flow rate of approximately 100 ml/30 seconds. A suspension of antibody coated beads specific to Giardia (500 μl) was added to the reservoir and the electrical power was turned on at 60 volts/50 Hz.

Circulation was continued for 60 minutes and current adjusted to 75 mA. Following this, excess beads were run to waste together with a 20 ml wash to PBT. The beads, prior to coating, were as described in Example 1.

A spike of Giardia cysts of known number in 25 ml was added to the reservoir and allowed to circulate for 60 minutes. At the end of this period the solid support was washed by running through 500 ml of PBT to waste. The flow as then halted and the Giardia bead complexes eluted from the solid phase using 20 ml PBS. This eluate was collected for determination of numbers of oocysts captured. To determine the number of cysts present, the liquid in each case was pushed through a membrane filter which was then stained and the numbers of Giardia determined by immunofluorescence. The results are shown in the table below:

| Run | Giardia Spike | Giardia Captured and Recovered | Percent Captured and Recovered |
| --- | --- | --- | --- |
| 1 | 584 | 405 | 69.3 |
| 2 | 584 | 221 | 37.8 |
| 3 | 423 | 246 | 58.2 |

EXAMPLE 5

Determination of Capture Efficiency of Cryptosporidium and Giardia.

Using the apparatus described in Example 3 25 ml PBT (Phosphate Buffered Saline+0.05% Tween 20) was circulated over the solid support at a flow rate of approximately 100 ml/30 seconds. A suspension of antibody coated beads specific for Cryptosporidium and Giardia (500 $\mu$l) was added to the reservoir and the electrical power was turned on at 60 volts/50 Hz. Circulation was continued for 60 minutes and current adjusted to 75 mA. Following this, excess beads were run to waste together with a 20 ml wash of PBT. Prior to antibody coating the beads were as described in Example 1.

A spike of combined Cryptosporidium and Giardia of known number in 25 ml PBT was added to the reservoir and allowed to circulate for 60 minutes. At the end of this period, the solid support was washed by running through 500 ml of PBT to waste. The flow as then halted and the cryptosporidium and Giardia complexes eluted from the solid phase using 20 ml PBS. This eluate was collected for determination of numbers of oocysts/cysts captured. To determine the number of cysts present, the liquid in each case was pushed through a membrane filter which was then stained and the numbers of organisms determined by immunofluorescence. The results are shown in the table below:

| | Spike | Spike | Organisms Captured and Recovered | | Percent Captured and Recovered | |
| --- | --- | --- | --- | --- | --- | --- |
| Run | C | G | C | G | C | G |
| 1 | 552 | 660 | 260 | 502 | 471 | 73.8 |
| 2 | 552 | 680 | 187 | 269 | 33.9 | 39.6 |
| 3 | 482 | 453 | 82 | 227 | 17.0 | 50.1 |

EXAMPLE 6

Capture of Cryptosporidium oocysts in river sediment.

Using the apparatus described above in Example 3 25 ml PBT (Phosphate Buffered Saline+0.05% Tween 20) was circulated over the solid support at a flow rate of approximately 100 ml/30 seconds. A suspension of antibody coated beads specific to Cryptosporidium (500 $\mu$l) was added to the reservoir and the electrical power was turned on at 60 volts/50 Hz. Circulation was continued for 60 minutes and current adjusted to 75 mA. Following this, excess beads were run to waste together with a 20 ml wash of PBT. The beads were as used in previous examples.

A spike of Cryptosporidium oocysts of known number in 25 ml PBT and river sediment (~100 NTU) was added to the reservoir and allowed to circulate for 60 minutes. At the end of this period, the solid support was washed by running through 500 ml of PBT to waste. The flow as then halted and the Cryptosporidium eluted from the solid phase using 20 ml PBS. This eluate was collected for determination of numbers of Cryptosporidium oocysts captured. To determine the number of oocysts present, the liquid in each case was pushed through a membrane filter which was then stained and the numbers of oocysts determined by immunofluorescence. The results are shown in the table below:

| Run | Oocysts | Oocysts Captured and Recovered | Percent Captured and Recovered |
| --- | --- | --- | --- |
| 1 | 515 | 111 | 21.5% |
| 2 | 515 | 104 | 29.2% |
| 3 | 492 | 115 | 23.3% |

EXAMPLE 7

Capture and Concentration of *Legionella pneumophila*.

Using the apparatus as described in Example 3 25 ml PBT (Phosphate Buffered Saline+0.05% Tween 20) was circulated over the solid support at a flow rate of approximately 100 ml/30 seconds. A suspension of antibody coated beads specific to *Legionella pneumophila* (500 $\mu$l) was added to the reservoir and the electrical power was turned on at 60 volts/50 Hz. Circulation was continued for 60 minutes and current adjusted to 75 mA. Following this, excess beads were run to waste together with a 20 ml wash of PET. The beads were as used previously.

A spike of *Legionella pneumophila* of known number in 25 ml was added to the reservoir and allowed to circulated for 60 minutes. At the end of this period, the solid support was washed by running through 500 ml of PBT to waste. The flow as then halted and the Legionella bead complexes eluted from the solid phase using 20 mls PBS. This eluate was collected for determination of numbers of bacteria captured. To determine the number of cells present, the liquid in each case was pushed through a membrane filter which was then stained and the numbers of Legionella determined by immunofluorescence. The results are shown in the table below:

| Run | Legionella Spike | Legionella Captured and Recovered | Percent Captured and Recovered |
| --- | --- | --- | --- |
| 1 | 1044 | 564 | 54% |
| 2 | 11854 | 4444 | 37.5% |
| 3 | 5611 | 3121 | 56.6% |

Many modifications and variations of the invention as illustrated and described above are possible within the broad scope of the invention. In particular, the invention may be applied to a wide range of analyte species. It will be of particular benefit where the analyte species is dilute and/or present in association with large amounts of particulate material, e.g. in the food industry for detecting organisms in foodstuffs such as cheese.

I claim:

1. A method of capturing a species from a liquid, comprising attracting magnetically attractable particles to a solid support by a magnetic field, wherein said particles have a substance on their surfaces which binds to said species, and contacting said particles on said solid support with said liquid to capture said species onto said particles on said solid support.

2. A method as claimed in claim 1, wherein said liquid is recirculated over said particles on said support to pass thereover repeatedly to capture said species on to said particles on said solid support.

3. A method as claimed in claim 1, wherein said solid support is of superparamagnetic or ferromagnetic material.

4. A method as claimed in claim 1, wherein said magnetic field is produced by an electromagnet and magnetic forces are reduced by deactivation of said electromagnet.

5. A method as claimed in claim 4, wherein said electromagnet comprises a C-shaped magnet core having a pole gap which receives said solid support and an electromagnet coil which is wound about said core at a location remote from said pole gap.

6. A method as claimed in claim 1, wherein said particles are ferromagnetic or superparamagnetic particles.

7. A method as claimed in claim 1 wherein said substance is selected from the group consisting of an antibody which binds specifically to an epitope on said species, a substance having an epitope which binds specifically to an epitope-binding site on said species, a nucleic acid or nucleic acid analogue which hybridizes specifically to said species which is a nucleic acid, a biotin moiety which binds specifically to a biotin-binding site on said species, and a biotin-binding protein which binds specifically to a biotin moiety on said species.

8. A method as claimed in claim 1, wherein said species to be captured is a water borne organism.

9. A method as claimed in claim 1, further comprising releasing said particles from said support by reduction of magnetic forces.

10. An assay method comprising:

capturing a species to be assayed or used in an assay, the capture being carried out by attracting magnetically attractable particles to a solid support by magnetic forces, which particles have an affinity for said species, and contacting said particles on said support with said liquid to capture said species on to said particles on said solid support, and detecting said captured species or using said captured species in detecting another species.

11. A method as claimed in claim 10, wherein said assay is an electro-rotation assay.

* * * * *